United States Patent
Pagliuca et al.

(10) Patent No.: US 9,347,079 B2
(45) Date of Patent: May 24, 2016

(54) PRODUCTION OF HIGHLY PURIFIED SODIUM HYALURONATE (HANA) WITH CONTROLLED MOLECULAR WEIGHT

(71) Applicant: Altergon Italia S.R.L., Pietradefusi (IT)

(72) Inventors: Maurizio Pagliuca, Pietradefusi (IT); Alessandro Ruggiero, Pietradefusi (IT); Felice Volpe, Pietradefusi (IT)

(73) Assignee: ALTERGON ITALIA S.R.L., Pietradefusi (AV) (IT)

(*) Notice: Subject to any disclaimer, the term of this patent is extended or adjusted under 35 U.S.C. 154(b) by 0 days.

(21) Appl. No.: 14/412,448

(22) PCT Filed: Jun. 14, 2013

(86) PCT No.: PCT/EP2013/062360
§ 371 (c)(1),
(2) Date: Jan. 1, 2015

(87) PCT Pub. No.: WO2014/005822
PCT Pub. Date: Jan. 9, 2014

(65) Prior Publication Data
US 2015/0152459 A1 Jun. 4, 2015

(30) Foreign Application Priority Data
Jul. 5, 2012 (IT) .................. MI2012A1184

(51) Int. Cl.
C12P 19/26 (2006.01)
C12N 1/20 (2006.01)
C12R 1/46 (2006.01)

(52) U.S. Cl.
CPC . C12P 19/26 (2013.01); C12N 1/20 (2013.01); C12R 1/46 (2013.01)

(58) Field of Classification Search
CPC .............. C12P 19/26; C12N 1/20; C12R 1/46
See application file for complete search history.

(56) References Cited

U.S. PATENT DOCUMENTS

| | | | |
|---|---|---|---|
| 6,454,946 B1 * | 9/2002 | DeFrees | 210/653 |
| 7,091,008 B1 * | 8/2006 | DeAngelis et al. | 435/84 |
| 8,927,234 B2 * | 1/2015 | Hashimoto et al. | 435/84 |
| 2010/0137579 A1 * | 6/2010 | Huang et al. | 536/123.1 |

FOREIGN PATENT DOCUMENTS

| | | | | |
|---|---|---|---|---|
| CN | 101935678 | * | 1/2011 | ............ C12P 19/04 |
| CN | 102242165 | * | 11/2011 | ............ C13P 19/04 |
| JP | 2012191901 | * | 3/2011 | ............ C12P 19/26 |

OTHER PUBLICATIONS

M. Stankovska et al Biomacromolecules, 2006, 7(3) 659-668 "Degradative Action of Reactive Oxygen Species on Hyaluronan".*
Zhou et al, "Separation of hyaluronic acid from fermentation broth by tangential flow microfiltration and ultrafiltration", Biotechnology letters, vol. 30 2008 493-496.*
Schiraldi et al., "Biotechnological Production and Application of Hyaluronan", Biopolymers, 2010, Scyo, 387-412.
Schiraldi et al., "Hyaluronic Acid Degradation During Initial Steps of Downstream Processing", Biocatalysis and Biotransformation, vol. 28, 2010, 83-89.
Rangaswamy et al., "An Efficient Process for Production and Purification of Hyaluronic Acid from *Streptococcus equi* Subsp. *zooepidermicus*", Biotechnology Letters, vol. 30, 2008 493-496.
Zhou, et al., "Separation of Hyaluronic Acid from Fermentation Broth by Tangential Flow Microfiltration and Ultrafiltration", Separation and Purification Technology, vol. 52, 2006, 29-38.
Deangelis, "Glycosaminoglycan Polysaccharide Biosynthesis and Production: Today and Tomorrow", Applied Microbiology and Biotechnology, vol. 94, Mar. 6, 2012, 295-305.
Schiraldi, et al., "Application of a 22L Scale Membrane Bioreactor and Cross-Flow Ultrafiltration to Obtain Purified Chondroitin", Biotechnology Progress, vol. 28, Jun. 22, 2012, 1012-1018.
Patil, et al., "Screening for Pharmaceutically Important Exopolysaccharide Producing Streptococci and Partial Optimization for EPS Production", Current Trends in Biotechnology and Pharmacy, vol. 3, 2009 329-340.
Marcellin, et al. "Understanding Plasmid Effect on Hyaluronic Acid Molecular Weight Produced by *Streptococci equi* Subsp. *ziooepidemicus*", Metabolic Engineering, vol. 12, 2010, 62-69.
SK 507 5-2 009, Contipro, C. Jul. 6, 2011.
"A Continually Evolving Company", Altergon Company Brochure, pp. 1-20.
Search Report and Written Opinion of PCT/EP2013/062360, Sep. 2, 2013.
Corrected Search Report for PCT/EP2013/062360, Sep. 16, 2013.

* cited by examiner

*Primary Examiner* — Louise W Humphrey
*Assistant Examiner* — Stephen A Perkins
(74) *Attorney, Agent, or Firm* — Silvia Salvadori, P.C.; Silvia Salvadori

(57) ABSTRACT

Disclosed is a process for the production of sodium hyaluronate with a molecular weight of between 60 and 2400 kDa and low polydispersity (1.4 $M_w/M_n$), which comprises: a) a step of fermentation of *Streptococcus equi* subsp. *Zooepidemicus* CNCM 1-4645 in a suitable culture medium; b) a step of ultrafiltration of the cell-free filtered solution; by concentrating and diafiltering the solution under differential pressure conditions ($\Delta P$) of 1.0-5.0 bar(g) and transmembrane pressure (TMP) of 0.5-4 bar(g).

5 Claims, 1 Drawing Sheet

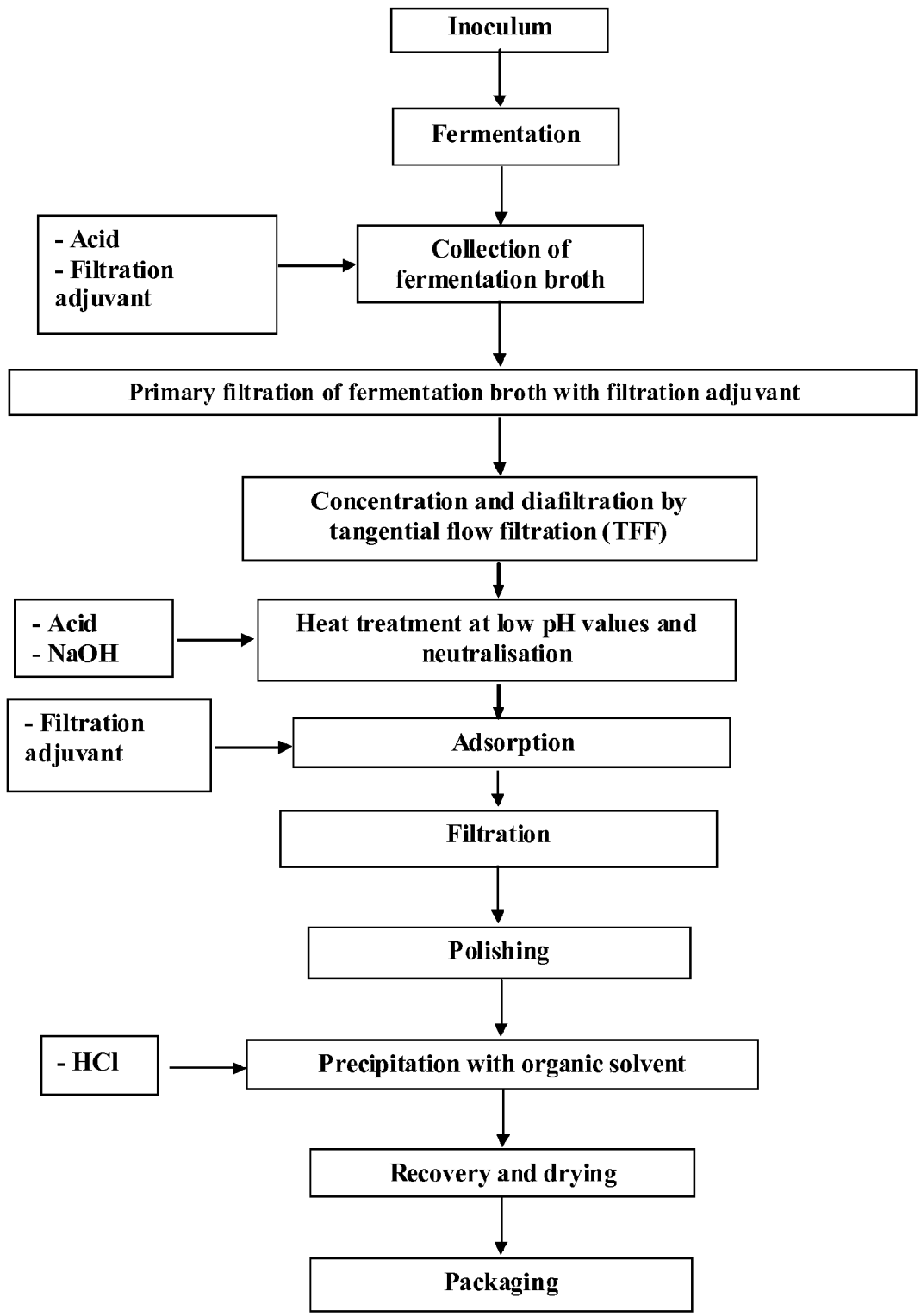

PRODUCTION OF HIGHLY PURIFIED SODIUM HYALURONATE (HANA) WITH CONTROLLED MOLECULAR WEIGHT

This application is a U.S. national stage of PCT/EP2013/062360 filed on 14 Jun. 2013, which claims priority to and the benefit of Italian Application No. MI2012A001184 filed on 5 Jul. 2012, the contents of which are incorporated herein by reference in their entireties.

The present invention relates to a process for the production of hyaluronic acid sodium salt which is highly purified by large-scale fermentation of a micro-organism of the genus *Streptococcus*.

FIELD OF INVENTION

The invention relates to processes for the production of highly purified sodium hyaluronate, and in particular to processes including a fermentation step.

By the process according to the invention, HANa is produced in compliance with current purity, safety and consistency standards. To obtain a high degree of purity, a medium containing no ingredients of animal origin is used in the process.

Due to the porosity and small size of its particles, the HANa obtained by the process claimed herein dissolves more rapidly than other HANas of animal and fermentation origin, leading to a considerable reduction in manufacturing time and costs. Moreover, the high purity of the material enables it to be sterilised subsequently without any significant loss of molecular weight. The advantages of this novel manufacturing process are therefore absolute safety, high purity profiles, and low thermolability; rapid dissolution and simple filterability to prepare solutions; and the reproducibility of the molecular weight, which is associated with low polydispersity.

PRIOR ART

Hyaluronic acid (HA) is a glycosaminoglycan present in nature, which consists of a linear polymer with a molecular weight of 50,000 to 13,000,000 daltons. It is a polysaccharide formed by repeating units of glucuronic acid and N-acetylglucosamine, bonded by alternating β1-3 and β1-4 bonds. Hyaluronic acid is present in various connective tissues of animals, such as skin and cartilage. Some organs, such as the umbilical cord, synovial fluid, vitreous humour and rooster combs, are particularly rich in hyaluronic acid. Hyaluronic acid is also produced by various micro-organisms, such as *Streptococcus* Type A and C. Hyaluronic acid is present in all the body tissues, and performs many important functions. It promotes the release of nutrients and transport of toxins from cells which have no blood supply, such as those located in cartilage; without adequate amounts of HA, the joints would deteriorate and become fragile. Hyaluronic acid not only keeps the joints lubricated, but also stimulates fluid retention in other body tissues. In the skin and cartilage, the role of hyaluronic acid is to bind to water and preserve the tonicity and elasticity of the tissue. The viscous hyaluronic acid solution in the joint fluids acts as a lubricant, providing a protective environment for the cells.

Due to its hydrophilic nature and its rheological and lubricating properties, sodium hyaluronate is a biopolymer with a high added value which has a wide variety of medical applications, including skin hydration, osteoarthritis treatment, ophthalmic surgery, prevention of adhesions after abdominal surgery, and wound healing.

Novel uses of sodium hyaluronate are drug release, coatings/implants and therapeutic treatments, based on its ability to modify cell behavior. As the performance of the product formulated in many of said applications depends on the molecular weight (MW) of the biopolymer, the MW represents a characteristic of primary importance in the production of sodium hyaluronate.

There are two main methods of obtaining sodium hyaluronate: (i) extraction of hyaluronic acid from animal tissues (e.g. extraction from rooster combs); (ii) growth of micro-organisms and recovery of hyaluronic acid as a product of fermentation.

(i) Extraction from rooster combs is expensive and time-consuming and leads to serious problems, namely a reduction in quality due to contamination by the enzymes that degrade hyaluronic acid (HAase), and inflammatory reactions at the time of injection. The extraction processes are also characterised by a number of problems and by low yields, limited availability of the starting material, inability to control the characteristics of the end product (such as the molecular weight), and contamination risks deriving from viruses.

(ii) The production of sodium hyaluronate by fermentation of a suitable micro-organism represents an effective process in terms of costs. Numerous methods are described in the literature for the production and purification of sodium hyaluronate using fermentation technology. However, many of them commonly use quaternary ammonium salts to remove impurities, leading to lengthy precipitate re-dissolution times and the presence of quaternary ammonium salts in the end product. Moreover, said purification techniques are mainly based on different precipitation steps requiring extensive use of organic solvents, thus increasing the costs associated with the purification of the product and waste disposal.

US2010/0137579A1 discloses a process for the purification of hyaluronic acid of biological origin (*Streptococcus zooepidemicus*) which is suitable for medical uses, comprising diafiltration and ultrafiltration steps.

The publication Biopolymers, 2010, 387-412 describes a process for the biotechnological production of hyaluronic acid by fermentation of *Streptococcus zooepidermicus*, filtration through a carbon filter, ultrafiltration/diafiltration and sterilisation by microfiltration.

Separation and Purification Technology, 2006, 52, 29-38 describes a two-step tangential flow filtration process for the separation of hyaluronic acid from a fermentation broth. However, this method is not suitable for large-scale production of hyaluronic acid, and the latter does not reach a purity suitable for medical uses.

In view of the problems associated with the methods described, the importance of a sodium hyaluronate manufacturing process which is simple, easily applicable and able to remove impurities such as proteins, nucleic acids, endotoxins, metal ions, etc., is clear.

DESCRIPTION OF THE INVENTION

The invention relates to a process for the production of sodium hyaluronate with high yields by fermentation of *Streptococcus* bacteria under aerobic conditions in a growth medium enriched with a flow of air, subsequent separation of the bacteria from the resulting culture broth, and isolation of sodium hyaluronate from the culture broth.

DETAILED DESCRIPTION OF THE INVENTION

The present invention overcomes the above-mentioned problems with a process for the production of highly purified sodium hyaluronate by fermentation in a suitable nutrient medium under appropriate conditions, using a micro-organism of the species *Streptococcus equi*, sub-sp. *zooepidemicus* (mutant strain deriving from wild-type strain DSM no. 20727). The mutant strain was deposited under CNCM number I-4645 on 21.06.2012 in the Pasteur Institute's Collection Nationale de Cultures de Microorganismes (Paris).

During fermentation, the micro-organism produces hyaluronic acid, and releases it into the culture medium.

Hyaluronic acid is then recovered from the fermentation medium by reducing the viscosity of the solution with an acid, concentrating and purifying it, for example by ultrafiltration, checking and defining the molecular weight with a heat treatment with low pH values, further purification by adsorption with a suitable adsorption technique, precipitating sodium hyaluronate, for example by precipitation with organic solvents, filtering and drying the precipitate.

FIG. 1 schematically illustrates the above-identified process according to the present invention.

According to the invention, "high-molecular-weight sodium hyaluronate" means a sodium hyaluronate having an intrinsic viscosity $\geq 1.8$ m$^3$/Kg.

The micro-organism is grown in a bioreactor, in a suitable culture medium, under high stirring and aeration speed conditions.

The medium contains a sugar as the carbon source at a starting concentration ranging from 20 to 80 grams per liter, and 20 to 30 grams per liter of yeast extract and/or soya peptone.

The pH of the medium is kept constant in the 6.0 to 8.0 interval by continuous addition of a basic solution managed by a pH controller; the pH of the medium is preferably maintained at about 7.0 by continual addition of concentrated NaOH.

The growth of the bacteria is carried out under pressurised aerobic conditions, preferably with a high stirring speed. The air pressure is kept constant at about 0.6-1.0 bar gauge, and the aeration at about 0.8-1.2 air volumes per medium volume per minute.

The fermentation yields range from 5.0 to 10 g·L$^{-1}$ of sodium hyaluronate with an average molecular weight ranging from about 1.8 to about 3.0×10$^6$ daltons.

The duration of fermentation is about 7-12 hours, with a 1 to 5% v/v inoculum grown to 4.0-12.0 OD units measured at 600 nm. At the end of fermentation, the density of the biomass is equivalent to a turbidity of 8-16 OD units.

The most suitable culture medium has the following composition:

| | |
|---|---|
| Sucrose | 60-80 g·L$^{-1}$ |
| Glucose | 20-60 g·L$^{-1}$ |
| Yeast extract | 20-30 g·L$^{-1}$ |
| Peptone | 10-30 g·L$^{-1}$ |
| Monobasic sodium phosphate monohydrate | 2.0-4.0 g·L$^{-1}$ |
| Magnesium sulphate heptahydrate | 1.0-3.0 g·L$^{-1}$ |
| Potassium sulphate | 0.5-2.2 g·L$^{-1}$ |
| Non-silicone antifoaming agent | 0.2-1.0 g·L$^{-1}$ |
| Calcium chloride hexahydrate | 8.0-12.0 mg·L$^{-1}$ |
| Manganese sulphate monohydrate | 0.05-0.2 mg·L$^{-1}$ |
| Copper sulphate pentahydrate | 0.01-0.1 mg·L$^{-1}$ |
| Zinc chloride | 0.05-0.2 mg·L$^{-1}$ |
| L-Arginine | 40.0-60.0 mg·L$^{-1}$ |
| Monosodium glutamate | 2.0-6.0 g·L$^{-1}$ |

Sodium hyaluronate can be recovered by treating the medium to remove the micro-organism and other materials insoluble in the medium. The preferred method of removal, after adding acid to reduce the viscosity of the solution, is filtration with an inert filtration aid.

Sodium hyaluronate is then microfiltered through filter cartridges with a nominal rating of 0.6/0.2 micrometers (μm) to remove any residues of the filtration aid and the micro-organism.

The pH of the medium is then adjusted to about 7.0 by adding concentrated NaOH.

The filtrate, treated with the inert filtration aid, undergoes tangential flow filtration (TFF) to remove the residual ingredients with low molecular weight deriving from the fermentation step. The ultrafiltration treatment is performed with ultrafiltration membranes with a cut-off of 10-100 KDa, with highly purified water (HPW) as diafiltration buffer.

The diafiltered solution is then subjected to heat treatment with the addition of hydrochloric acid (2M) to reduce its molecular weight and intrinsic viscosity. At the end of the heat treatment the pH of the solution is adjusted to 7.0±1.0 by adding concentrated NaOH.

The product thus obtained, after the addition of sodium chloride (normally 0.7 M) is purified with a suitable filtration aid and then filtered.

The filtrate is then microfiltered through filter cartridges with a nominal rating of 0.2 micrometers (μm).

After the addition of hydrochloric acid (HCl), sodium hyaluronate can be precipitated with an organic solvent such as 96% v/v ethanol. After removal of the supernatant, 96% v/v ethanol is added to the precipitate. After removal of the supernatant, 96% v/v ethanol is added to this second precipitate. The precipitate thus recovered is then dried under vacuum to obtain a fine sodium hyaluronate powder. If desired, sodium hyaluronate can be produced with a defined molecular weight and intrinsic viscosity by conducting a heat treatment at low pH values according to the table set out below:

| Molecular weight (KDa) | Intrinsic viscosity (m$^3$·Kg$^{-1}$) | pH |
|---|---|---|
| 60-100 | 0.14-0.29 | 1.00-3.00 |
| 100-250 | 0.29-0.68 | 1.00-3.00 |
| 250-350 | 0.68-0.88 | 2.00-4.00 |
| 350-500 | 0.88-1.12 | 2.00-4.00 |
| 500-800 | 1.2-1.52 | 2.00-4.00 |
| 800-1000 | 1.52-1.75 | 3.00-5.00 |
| 1000-1400 | 1.75-2.14 | 3.00-5.00 |
| 1400-1800 | 2.14-2.47 | 3.00-5.00 |
| 1800-2400 | 2.47-2.92 | 3.00-5.00 |

The invention will be described in greater detail in the following example.

Example

Selection of Bacteria for High-Yield Production

*Streptococcus equi* subsp. *zooepidemicus* CNCM 1-4645 (mutant strain deriving from wild-type strain DSM number 20727, deposited in the DSMZ Microbial Collection) is used as HANa producing bacterium: the micro-organism is stored in 20% (v/v) glycerol in a vial and frozen (T←−70° C.).

The manufacturing process begins with thawing of a vial followed by streaking of the bacterial suspension in the plate on solid medium, and growth at 37° C. for 20-36 hours (Revitalisation Step). A colony taken from the plate is then resuspended in fresh culture medium in a test tube and incubated for 8-16 hours at 37° C. under stirring (100-300 rpm, Cell Expansion Step I). The test tube is then used as inoculum in two 5-liter Erlenmeyer flasks containing 2 liters of sterile culture medium. The flasks are incubated for 8-16 hours at 37° C. under stirring (100-300 rpm, Cell Expansion Step II). The cell suspension obtained is then used for inoculation.

Production Fermentation

After inoculation into the sterile culture medium, the production fermentation is carried out at 30-40° C. and pH 7.0±1.0 with aeration of 1500 L·min$^1$, overpressure of 0.6-1.0 bar gauge, and stirring at 200-300 rpm. The pH value is kept constant in the specific range by adding concentrated NaOH. During fermentation, hyaluronic acid forms as part of the cell capsule, and is gradually released in soluble form into the fermentation medium.

Filtration and Microfiltration

The fermentation culture broth is transferred to a tank where an acid is added to make it less viscous, and an inert filtration aid is added to obtain the higher rate of flow necessary for the required degree of clarification. When the packing step has been completed, the cell suspension is conveyed by a pump to a pressurised filter and filtered; the panel that forms is retained by the filter plates, while the filtrate is recovered for the subsequent steps.

The product thus obtained is microfiltered to remove any aid or cell residues by filtering it, with normal flow filtration (NFF), through filter cartridges with a nominal rating of 0.6/0.2 micrometers (m).

Neutralisation and Ultrafiltration

After the filtration and microfiltration (MF) steps, a cell-free filtered solution of sodium hyaluronate is obtained, which can be purified. The first step is to collect the product in a storage tank to which concentrated NaOH is added to restore the pH value to about 7.

A membrane tangential flow ultrafiltration (TFF) system is used to concentrate and purify the product. The membranes used (cassettes or hollow fibre modules) are made of a material compatible with the process, preferably polyethersulphone or polypropylene, and have a cut-off of 10-100 kDa, preferably 30 kDa. The operating intervals of the ultrafiltration process parameters are: transmembrane pressure (TMP) 0.5-4.5 bar(g) and differential pressure (ΔP) 1.0-5.0 bar(g). The supernatant is concentrated up to 3-5 times the initial volume to eliminate the majority of low-molecular-weight contaminants. The retentate containing sodium hyaluronate is diafiltered up to 5-7 volumes with highly purified water to remove the remaining low-molecular-weight contaminants. The diafiltration terminates when a conductivity value below 300 µS·cm$^{-1}$ is reached.

Heat Treatment at Low pH Values and Neutralisation

The concentrated, diafiltered product is heated under stirring in a process thank thermostated in a temperature range of 50-65° C., and the pH is adjusted to the value of 1-5 by adding hydrochloric acid. The solution is then incubated under said conditions until the required molecular weight is obtained. Under these conditions, the sodium hyaluronate molecules break down at random without forming by-products. The heat treatment is terminated by adjusting the pH to a value of 7.0±1.0 with concentrated NaOH and cooling to a temperature of about 25.0° C.

Adsorption with Activated Carbon, Filtration and Polishing

A salt is added to the ultrafiltered solution to reduce its viscosity, and a filtration aid is used to remove endotoxins. To remove the endotoxins effectively, the solution is stirred for at least 2-4 hours and then filtered to remove the filtration aid. The filtrate is microfiltered by normal flow filtration to eliminate any residues of filtration aid.

Precipitation

After adding hydrochloric acid (e.g. 2M) to neutralise the solution, an organic solvent (such as 96% v/v ethanol) is added to the sodium hyaluronate solution. The water-soluble organic solvent is preferably added in the range of 1.2-2.8 volumes of the sodium hyaluronate solution. To precipitate and sediment sodium hyaluronate effectively by adding an organic solvent to the sodium hyaluronate solution, it is preferable to leave it to sediment for at least 3-7 hours after adding the organic solvent.

The precipitated sodium hyaluronate obtained at this step, from removal of the supernatant, is washed by adding fresh organic solvent. The sodium hyaluronate precipitate obtained at this second step, after removal of the supernatant, is resuspended in fresh organic solvent.

Recovery and Drying

The sedimented sodium hyaluronate is recovered and filtered. A final drying step is performed under vacuum to obtain a very fine powder.

Sodium hyaluronate thus obtained is suitable to produce preparations characterised by the absence of pyrogenicity and inflammatory activity.

The invention claimed is:

1. A process for the manufacture of sodium hyaluronate with defined molecular weight ranging from 60 to 2400 kDa and a polydispersity of 1.4 $M_w/M_n$ which comprises:
   a) a fermentation step of *Streptococcus equi* subsp. *zooepidemicus* CNCM I-4645 in a culture medium;
   b) an ultrafiltration step of the cell-free filtered solution with membranes of polyethersulfone or polypropylene with a cut-off of 10-100 kDa, concentrating and diafiltering the solution in differential pressure conditions (ΔP) from 1.0 to 5.0 bar(g) and at transmembrane pressure (TMP) from 0.5 to 4.5 bar(g); and
   c) a heat treatment step in a temperature range of between 50° C. to 65° C.

2. The process according to claim 1 wherein the fermentation step is carried out in batch procedure to give a concentration of hyaluronic acid of 5-10 g/L after 7-12 hours.

3. The process according to claim 1 wherein the fermentation step is carried out in aerobic conditions at the pressure of 0.6-1.0 bar gauge and an aeration condition of about 0.8-1.2 volumes of air per volume of medium per minute.

4. The process according to claim 1 wherein the culture medium has the following composition:
   Sucrose 60-80 g/L
   Glucose 20-60 g/L
   Yeast extract 20-30 g/L
   Peptone 10-30 g/L
   Monobasic sodium phosphate monohydrate 2.0-4.0 g/L
   Magnesium sulphate heptahydrate 1.0-3.0 g/L
   Potassium sulphate 0.5-2.2 g/L
   Non-silicone antifoam 0.2-1.0 g/L
   Calcium chloride hexahydrate 8.0-12.0 mg/L
   Manganese sulphate monohydrate 0.05-0.2 mg/L
   Copper sulphate pentahydrate 0.01-0.1 mg/L
   Zinc chloride 0.05-0.2 mg/L 1L-arginine 40.0-60.0 mg/L
   Sodium glutamate 2.0-6.0 g/L.

5. The process according to claim 1 wherein sodium hyaluronate is produced with a predefined molecular weight and intrinsic viscosity by carrying out heat treatment in a temperature range of between 50° C. to 65° C. at pH values according to the following table:

| Molecular weight (KDa) | Intrinsic viscosity (m³·kg⁻¹) | pH (UpH) |
| --- | --- | --- |
| 60-100 | 0.14-0.29 | 1.00-3.00 |
| 100-250 | 0.29-0.68 | 1.00-3.00 |
| 250-350 | 0.68-0.88 | 2.00-4.00 |
| 350-500 | 0.88-1.12 | 2.00-4.00 |
| 500-800 | 1.2-1.52 | 2.00-4.00 |
| 800-1000 | 1.52-1.75 | 3.00-5.00 |
| 1000-1400 | 1.75-2.14 | 3.00-5.00 |
| 1400-1800 | 2.14-2.47 | 3.00-5.00 |
| 1800-2400 | 2.47-2.92 | 3.00-5.00 |

\* \* \* \* \*